United States Patent [19]

Smith, Jr. et al.

[11] 4,447,668

[45] May 8, 1984

[54] PROCESS FOR PRODUCING HIGH PURITY ISOOLEFINS AND DIMERS THEREOF BY DISSOCIATION OF ETHERS

[75] Inventors: Lawrence A. Smith, Jr., Bellaire; Edward M. Jones, Jr., Friendswood; Dennis Hearn, Houston, all of Tex.

[73] Assignee: Chemical Research & Licensing Company, Houston, Tex.

[21] Appl. No.: 496,983

[22] Filed: May 25, 1983

Related U.S. Application Data

[63] Continuation of Ser. No. 363,053, Mar. 29, 1982, abandoned.

[51] Int. Cl.³ ............................................. C07C 1/00
[52] U.S. Cl. ..................................... 585/639; 585/510; 585/515
[58] Field of Search .................... 585/639, 510, 515

[56] References Cited

U.S. PATENT DOCUMENTS

| | | | |
|---|---|---|---|
| 2,403,672 | 7/1946 | Matuszak | 585/664 |
| 3,091,586 | 5/1963 | Pappas et al. | 208/210 |
| 3,121,124 | 2/1964 | Verdol | 585/639 |
| 3,170,000 | 2/1965 | Verdol | 585/640 |
| 3,270,081 | 8/1966 | Verdol et al. | 585/327 |
| 3,317,593 | 5/1967 | Enk et al. | 562/206 |
| 3,531,539 | 9/1970 | Tidwell | 585/251 |
| 3,629,478 | 12/1971 | Haunschild | 203/38 |
| 3,634,534 | 1/1972 | Haunschild | 585/834 |
| 3,726,942 | 4/1973 | Louder | 568/697 |
| 3,825,603 | 7/1974 | Massie | 568/630 |
| 3,846,088 | 11/1974 | Brown et al. | 44/56 |
| 3,940,450 | 2/1976 | Lee | 568/697 |
| 4,100,220 | 7/1978 | Bowman et al. | 585/515 |
| 4,198,530 | 4/1980 | Wentzheimer et al. | 568/697 |
| 4,232,177 | 11/1980 | Smith | 585/324 |

Primary Examiner—Curtis R. Davis
Attorney, Agent, or Firm—Kenneth H. Johnson

[57] ABSTRACT

Alkyl tertiary butyl ether or alkyl tertiary amyl ether is dissociated by vapor phase contact with a cation acidic exchange resin at temperatures in the range of 150° to 250° F. at LHSV of 0.1 to 20 to produce a stream consisting of unreacted ether, isobutene or isoamylene and an alcohol corresponding to the alkyl radical. After the alcohol is removed, the ether/isoolefin stream may be fractionated to obtain a high purity isoolefin (99+%) or the ether/isoolefin stream can be contacted in liquid phase with a cation acidic exchange resin to selectively dimerize the isoolefin in a highly exothermic reaction, followed by fractionation of the dimerization product to produce high purity diisoolefin (97+%). In the case where the alkyl is $C_3$ to $C_6$ and the corresponding alcohol is produced on dissociation of the ether, combined dissociation-distillation may be carried out such that isoolefin is the overhead product and alcohol the bottom.

34 Claims, 2 Drawing Figures

PROCESS FOR PRODUCING HIGH PURITY ISOOLEFINS AND DIMERS THEREOF BY DISSOCIATION OF ETHERS

The Government of the United States of America has certain rights in this invention pursuant to Contract No. DE-FC07-80CS40454 awarded by the U.S. Department of Energy.

This application is a continuation of application Ser. No. 363,053 filed Mar. 29, 1982 now abandoned.

BACKGROUND OF THE INVENTION

1. Field of the Invention

The invention relates to a method for producing high purity tertiary $C_4$ and $C_5$ olefins by the dissociation of the corresponding alkyl ethers and the subsequent dimerization of the olefins to produce high purity dimers thereof. Namely the present invention relates to a method for producing high purity isobutene and diisobutene by the dissociation of alkyl tertiary butyl ether and the dimerization of the isobutene from the dissociation and a similar dissociation of alkyl tertiary amyl ether and dimerization of the isoamylenes from the dissociation.

2. Related Art

Isobutene is a component of a $C_4$ refinery stream. The separation of isobutene from the corresponding normal olefins by simple fractionation is extremely difficult, because of the closeness of their boiling points. In commercial processes as generally practiced, called the cold acid process, the isoolefin is selectively absorbed by sulfuric acid and the resulting isoolefin-containing sulfuric acid extract is then diluted and heated or treated with steam to separate the isoolefin. The diisobutene is a by-product of this separation.

The separation is achieved by virtue of the solubility of the isobutene in sulfuric acid. The remainder of the $C_4$ stream is recovered for further treatment to separate the n-butenes and n-butanes. Although the sulfuric acid is highly selective for the isobutene, there will be some copolymer dimer from the iso- and n-butene formed.

The isoamylene is similarly difficult to separate from streams containing normal $C_5$ olefins.

U.S. Pat. No. 4,242,530 discloses the removal of isobutene from a $C_4$ stream and the production of diisobutene in a "catalytic distillation process", which uses a catalyst structure, in this case cation acid exchange resin in wire supported cloth bags, as a catalyst and distillation component to carry out the reaction and fractionation concurrently. This is an excellent means to remove isobutene and to produce a diisobutene equal to that produced by the cold acid process.

The "catalytic distillation process" has also been shown to be a useful method for reacting an alcohol and isobutene to produce ether, e.g., methanol to produce methyl tertiary butyl ether (MTBE), U.S. Pat. Nos. 4,232,177 and 4,307,254. The etherification is known to be a reversible reaction and is forced to completion by the removal of product concurrently with the reaction. Similarly, U.S. Pat. No. 4,232,177 shows the use of the catalytic distillation process to dissociate ether, i.e., MTBE to produce methanol and isobutene and diisobutene. The catalytic fractionation is a combination liquid phase/vapor phase process just as any distillation is. The product isobutene, however, is contaminated with methanol since isobutene forms an azeotrope with methanol.

Commonly assigned U.S. patent application, Ser. No. 234,653 filed Feb. 17, 1981, discloses the preparation of the ethers of isobutene and isoamylene in the catalytic distillation process using $C_1$ to $C_6$ alcohols.

It has now been found that the dissociation of alkyl tertiary butyl ether and alkyl tertiary amyl ether is best carried out in vapor phase, although in some cases the catalytic distillation environment is overall more efficient.

Both isobutene and diisobutene are of significant value having diverse applications; for example, isobutene is one of the comonomers for butyl rubber and diisobutene is an intermediate in the preparation of detergents. Isoamylenes have use as tackifiers in rubber manufacturer, in insecticides and demulsifiers for tertiary recovery of oil, and the diisoamylene is useful as gasoline blending stock.

SUMMARY OF THE INVENTION

In its broadest sense, the present invention relates to the dissociation of alkyl tertiary butyl ether or alkyl tertiary amyl ether which is at least partially in the vapor phase.

In the present process in one embodiment the following steps are carried out in various permutations to obtain high purity diisobutene:

(1) vaporizing a feed stream of alkyl tertiary butyl ether, (2) passing said feed stream in a vaporized state through a fixed bed cation acidic exchange resin whereby said ether is at least partially dissociated and the dissociation product stream from the catalyst bed contains isobutene, alcohol corresponding to the alkyl radical and unreacted alkyl tertiary butyl ether, (3) removing said alcohol from said dissociation product stream, (4) passing said alcohol depleted product stream in liquid phase into contact with a cation acidic exchange resin, to form diisobutene product, and (5) separating diisobutene and unreacted alkyl tertiary butyl ether from diisobutene product.

As an alternative to carrying out step 4 and 5, the liquified stream from step 3, i.e., condensed stream which is now predominately isobutene and unreacted ether feed, can be fractionated to produce a high purity isobutene. The unreacted ether is easily recycled to the feed to the dissociation column.

In another embodiment the following steps are carried out in various premutations to obtain high purity diisoamylene:

(1) vaporizing a feed stream of $C_1$ to $C_6$ alkyl tertiary amyl ether, (2) passing said feed stream in a vaporized state through a fixed bed cation acidic exchange resin whereby said ether is at least partially dissociated and the dissociation product stream from the catalyst bed contains isoamylene, alcohol corresponding to the alkyl radical and unreacted alkyl tertiary amyl ether, (3) removing said alcohol from said dissociation product stream, (4) passing said alcohol depleted product stream in liquid phase into contact with a cation acidic exchange resin, to form diisoamylene product and (5) separating isoamylene and unreacted alkyl tertiary amyl ether from diisoamylene product.

As an alternative in this embodiment, steps 4 and 5 are omitted and the liquified stream from step 3, i.e., condensed stream which is now predominately isoamylene and unreacted ether feed, can be fractionated to produce a high purity isoamylene.

In an alternative embodiment wherein a dissociation/distillation is concurrently carried on, the materials in the distillation column reactor are in the vapor and liquid phases, as with any distillation. This method of conducting the dissociation is advantageous when the alcohol formed does not azeotrope with the isobutene or isoamylene. Under that provision the dissociation and separation of alcohol from the dissociation product stream is carried out concurrently in the distillation column reactor.

In this embodiment a $C_3$–$C_6$ alkyl tertiary butyl ether (or $C_3$–$C_6$ alkyl tertiary amyl ether) is fed to a distillation column reactor in a feed zone. The feed zone is at the lower end of a fixed bed acid cation resin packing (the term "lower end" includes below the packing). The catalyst packing as described herein allows concurrent catalytic dissociation of the ether and fraction of the resultant mixture using the catalyst packing as the distillation packing. The ether dissociates into an alcohol corresponding to the alkyl group, i.e., a $C_3$–$C_6$ alcohol and isobutene (or isoamylene). Methanol and ethanol (from methyl tertiary alkyl ethers and ethyl tertiary alkyl ethers respectively) form azeotropes with the isoolefin, hence a fractionation will always produce an isoolefin fraction contaminated with alcohol which needs to be removed, e.g., with water wash, hence the straight vapor phase dissociation with its favorable dissociation equilibrium is preferred. However, with the $C_3$–$C_6$ tertiary $C_4$ or $C_5$ ethers, which produce non azeotroping alcohols on dissociation, the loss in dissociation rate is more than compensated by the elimination of a separate alcohol removal step. The concurrent fractionation of the dissociated $C_3$–$C_6$ tertiary $C_4$ or $C_5$ ethers, produces an overhead, (above the catalyst packing) high purity isobutene or isoamylene. The bottoms contain alcohol and may contain some unreacted ether. This material may be used as a feed to an etherification reaction to produce more of the ether to be used for the dissociation.

The dissociation of alkyl tertiary amyl ether results in the production of two isomers of isoamylene, i.e., 2-methyl butene-1 and 2-methyl butene-2, which are both desirable.

DETAILED DESCRIPTION OF THE INVENTION

Figure 1:
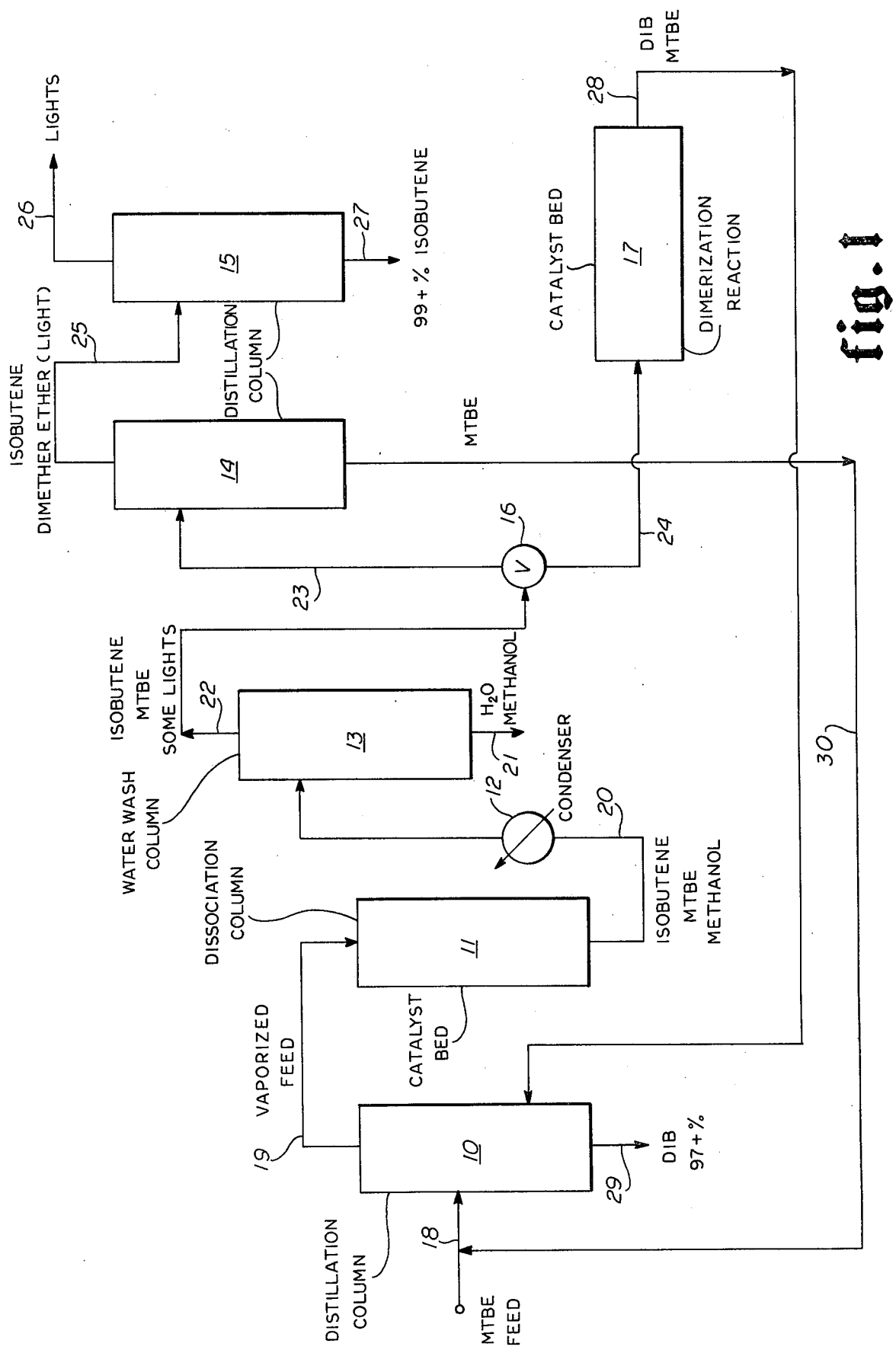
FIG. 1 shows a schematic representation of a process for producing either high purity isobutene or diisobutene.

The etherification reaction is known to be reversible. The reaction is reversible in the liquid phase, mixed liquid and vapor phase (the catalytic distillation) and in vapor phase; however, it has been observed that the dissociation equilibrium concentrations appear to be about three times more favorable towards producing isobutene (or isoamylene) in the vapor phase as compared to a liquid phase system.

The present dissociation is preferably carried out in vapor phase, at a temperature which will maintain the reactants in the vapor phase rather than in a distillation, i.e., reflux state.

The preparation of the ether from isobutene or isoamylene and its subsequent dissociation according to the present process is not redundant as it may at first appear. Isobutene is a component of $C_4$ refinery streams. The separation of the isobutene from such streams in a pure state by fractionation, because of the closeness of the component boiling points, is extremely difficult and even more so if extremely high purity isobutene is desired. However, the isobutene is readily and selectively reacted with $C_1$–$C_6$ alcohols to form the ethers which can be separated from the other $C_4$ components by conventional distillation. Thus, when the ethers are dissociated according to the present invention extremely high purity isobutene is produced, that is isobutene with very little of any other $C_4$ present. The same considerations apply to the isoamylene.

The alkyl tertiary butyl ether or alkyl tertiary amyl ether may be produced by any of the methods known in the art and should itself be a relatively pure feed to the present dissociation, quite obviously, preferably at least 97 wt.% ether and more preferably at least about 99 wt.% ether.

The cation acidic exchange resin is employed in a fixed bed. A fluidized or moving bed would operate; however, the attrition of the catalyst particles would render such a system unrealistic and at the least undesirable. A catalyst packing system and catalyst structures as described in U.S. Pat. No. 4,215,011 may be used in the present dissociation and provides a convenient means of handling the catalyst packing. However, in the strictly vapor phase system, since the dissociation is in the vapor phase and not in a distillation mode, the openness of these structures is not required and the resin beads packed into a reactor provide adequate open space to pass the vapor through without inordinately high pressure drops.

In the vapor phase system it is convenient to pack or load the catalyst, which is usually in granular or bead form, into a heat exchanger having means to introduce heat thereto in order to maintain the vapor phase and desired temperatures. The feed to dissociation reactor is preferably a down flow, so as not to fluidize the catalyst bed which would result in attrition of the catalyst. In the event that the catalyst does become fouled with heavy by-products, these may be removed by washing the catalyst with the liquid feed.

In one embodiment using the catalytic distillation packing catalyst and up flow vapor stream (distillation) a small counter flow stream of the ether feed stream was fed at the top of the catalyst packing in order to wet the catalyst and remove any by-product build-up.

The most readily available alkyl tertiary butyl ether is methyl tertiary butyl ether (MTBE), which is widely used as an octane improver for gasoline; however, for the specialized purpose of the present invention other alcohols can be produced in the processes used to etherify isobutene or isoamylene, i.e., $C_1$ to $C_6$ alcohols can be used as taught in copending commonly assigned application. Ser. No. 234,653, filed Feb. 17, 1981, which is incorporated herein in its entirety. These alternative ethers may have other uses, but the benefit that some offer to the present process, justifies their manufacture. The alcohols derived from the dissociation of the present ethers are monohydric, e.g., methanol, ethanol, isopropanol, tertiary butanol and the like.

In a variation the alcohol portion of the present ethers may themselves be ethers, these alcoholic ethers are more stable than the tertiary alkyl ethers which are being dissociated and thus are recoverable. Suitable alkoxy alcohols, which may be used to produce the ethers for dissociation, include 2-methoxy ethanol, 2-ethoxy ethanol, 2-isopropyl ethanol, isobutoxy ethanol, 2-ethoxy-1-propanol and the like. Particularly preferred are alkoxy alcohols of the general formula $$R_1-O-R_2-OH$$

wherein $R_1$ is a hydrocarbon radical having one to four carbon atoms and $R_2$ is a hydrocarbon radical having one to two carbon atoms.

The $C_3$ and higher alcohols produced by dissociation of 3-6 carbon atom alkyl tertiary ethers do not azeotrope with isobutene or isoamylene. For example, by using normal propyl tertiary butyl ether in the process, the alcohol dissociation product, N-propyl alcohol does not form an azeotrope with isobutene dissociation product and is easily separated therefrom in a fractionation.

Thus, the combined or concurrent dissociation and distillation produces a very high purity overhead and a bottom fraction of alcohol. The isobutene or isoamylene overhead can be recovered as such or dimerized as described.

The separation of methanol (product from MTBE) from isobutene is not difficult and may be readily obtained by water washing of the dissociation product. The wash water, however, should be further treated for recycle and the methanol recovered, if the process is to economically operated.

The dimerization of the isobutene to diisobutene (or isoamylene to diisoamylene) is carried out in liquid phase using the same type of catalyst as used in the dissociation. The physical arrangement can be the same as in the dissociation reactor; however, it is essential that means be provided for removal of heat from the dimerization, which is highly exothermic. The presence of the undissociated ether presents no problem and serves as a diluent to aid in control of the dimerization reaction. The highly exothermic nature of the dimerization indicates a diluent is necessary. It has been found that the ether as a diluent is superior to other diluents such as hexane, in that the process is more selective to diisoolefin. It has also been observed that there is some further dissociation of the ether present. Since the dimerization is highly selective the resultant product from the dimerization reactor (in which ether is present) may contain some alcohol as a result of the dissociation which is easily removed by a water wash or a distillation (topped).

The stream from the dimerization contains principally diisoolefin and ether (if present in the feed thereto or some other diluent if used) which is fractionated to produce high purity diisoolefin. Very conveniently the product from the dimerization can be fractionated in the vaporizer for the feed to the dissociation reactor (vapor phase embodiment). The intrinsic heat in the dimerization product stream is thereby employed to vaporize the ether feed and the diisoolefin is recovered as bottoms.

The temperature in the dissociation reactor is at or above the vaporization temperature of the ether (e.g., MTBE) at the pressure of the reactor. The pressure in the reactor can be subatmospheric up to a pressure where the boiling point of the ether is about 250° F., generally about 10 to 60 psig. The temperature in the dissociation reactor is determined by the desired rate of dissociation of the ether, (i.e., higher temperature favors dissociation) and by the decomposition temperature of the catalyst. With these points in view the normal operating temperature is in the range of 150° F. to 250° F.

In the concurrent dissociation distillation, the temperature in the distillation column reactor is controlled (as is every distillation) by the boiling point of the liquid mixture present at the pressure of the system.

The success of the catalytic distillation approach lies in an understanding of the principles associated with distillation. First, because the reaction (dissociation) is occurring concurrently with distillation, the isobutene or isoamylene is removed from the reaction zone as quickly as it is formed. This removal of the isoolefin minimizes the reverse reaction to form the ether and chaining to form polymer. Second, because all the isoolefin is boiling, the temperature of the reaction is controlled by the boiling point of the liquid mixture at the system pressure. The heat of reaction simply creates more boil up, but no increase in temperature. Third, the reaction has an increased driving force because the reaction products have been removed and can not contribute to a reverse reaction (LeChatelier's Principle).

As a result, a great deal of control over the rate of reaction and distribution of products can be achieved by regulating the system pressure. Also, adjusting the through-put (residence time=liquid hourly space velocity$^{-1}$) gives further control of product distribution and degree of isoolefin removal.

The dissociation of the specified alkyl tertiary butyl ether to form isobutene and alcohol is an equilibrium reaction according to the following equation:

$$RTB \underset{K_2}{\overset{K_1}{\rightleftarrows}} IB + alc.$$

The rate constants $K_1$ and $K_2$ are both temperature dependent, however, the dissociation reaction (RTBE$-K_1\rightarrow$IB+alc.) increases much more rapidly with temperature rise than does the reverse reaction (IB+alc.$-K_2\rightarrow$RTBE). The same is true for the alkyl tertiary amyl ether also.

Thus, the temperatures within the ranges specified elsewhere herein are preferred for this embodiment.

The dissociation rate increase with temperature coupled with the concurrent and continuous removal of isoolefin as a fractionated overhead and the elimination of a separate step for removal of alcohol from the isoolefin makes the catalytic distillation advantageous for the dissociation of non azeotroping alcohols. This advantage is achieved by reducing initial equipment (elimination of a water wash tower and associated alcohol recovery systems) and elimination of the energy requirements for operating the water wash and alcohol recovery systems. Furthermore, by eliminating additional equipment the operation of the system is simplified.

The dimerization reactor is operated at a pressure to maintain the liquid phase under the condition of temperature. As indicated above, the dimerization reaction is exothermic, however, for the benefit of the catalyst, the temperature is maintained below about 250° F., generally about 150° to 250° F.

The alkyl tertiary butyl ether feed to the system (i.e., the dissociation column) should contain at least 50 weight % of the ether up to 100 wt.%. The balance of the feed is preferably inert.

Referring to FIG. 1, a schematic system is shown, which can be used to produce either high purity diisobutene or high purity isobutene.

A feed stream 18, containing 98 wt.% methyl tertiary butyl ether (MTBE) is fed to distillation column 10 operated to vaporize the MTBE. The vaporized overhead 19 passes into dissociation vessel or column 11, which is preferably a heat exchanger with a cation exchange resin, for example Amberlyst 15 (Rohm & Haas Company, Philadelphia, Pa.) packed into one portion of the heat exchanger and operably connected to the vapor exit 19. Means (not shown) is provided to add heat to the dissociation column 11 to maintain the temperature and vapor phase conditions. The rate of feed through the bed may be 0.1 to 20 LHSV (Liquid Hourly Space Velocity which is liquid volumes per volume of reactor containing catalyst per hour). In the present case the LHSV was 3. The material leaving the dissociation column 11 contains isobutene, MTBE and methanol. This is condensed in condenser 12 and passed via 20 into the water wash column 13 which is operated under pressure (>15 psig) to remove the methanol with $H_2O$, via 21. This stream may be fractionated to recover the methanol.

The overhead raffinate from the water wash column 13 is a stream of isobutene and MTBE, which is substantially free of methanol. This material may be used either to produce diisobutene or to recover isobutene. As illustrated here a valve 16 is provided to send the crude isobutene stream to one or the other processing section.

The material from column 13 is fed through line 23 into distillation column 14, operated to fractionate the isobutene overhead and unreacted MTBE as the bottom which can be recycled via 30 to the feed 18.

The overhead 25 contains isobutene and some other materials such as dimethyl ether. This stream is sent to a final finish distillation column 15, where the lighter material including the dimethyl ether are taken off overhead and high purity 99+% isobutene is the bottoms product 27. It is believed that as a specification product the present process will produce a product purity not previously available.

By directing the raffinate stream 22 from tower 13 through line 24 into the catalyst bed dimerization reactor 17 a diisobutene product stream 28 is produced. This reactor is a liquid phase reactor and is preferably arranged as a heat exchanger, such that the line 24 communicates with the portion containing the catalyst. Since the reaction is highly exothermic a heat exchange medium is passed through the reactor to remove this heat. The reactor is operated at a pressure to maintain the liquid phase at the temperature of the reactor which is below 250° F., and preferably 170° to 230° F.

The stream 28 emitting from reactor 17 is a stream high in DIB and also containing unchanged MTBE. This stream is fed back to the distillation column 10 where the intrinsic heat from the dimerization is partially dissipated in vaporizing the MTBE. The diisobutene comes out as a 97+% bottoms product. This material will routinely be of a higher specification than currently available.

In order to further illustrate the operation of the process the various process streams from runs to produce the two products are set out in TABLE I. The amounts are in weight.

The feed of stream 22 via valve 16 to the dimerization reactor 17 is in no wise hampered by the presence of water in the stream.

TABLE I*

| | STREAM | | | | | | | | | |
|---|---|---|---|---|---|---|---|---|---|---|
| | 18 | 19 | 20 | 21 | 22 (23)(24) | 25 | 27 | 28 | 29 | 30 |
| DIB | | | | | | | | | | |
| Component | | | | | | | | | | |
| Isobutene | — | — | 37 | — | 37 | | | 11 | — | |
| Methanol | — | — | 16 | 16 | — | | | 1 | — | |
| MTBE | 98 | 98 | 45 | — | 45 | | | 42 | — | |
| DIB | 2 | 2 | 2 | | 2 | | | 30 | 30 | |
| ISOBUTENE | | | | | | | | | | |
| Component | | | | | | | | | | |
| Isobutene | — | — | 37 | — | 37 | 37 | 37 | | | — |
| Methanol | — | — | 16 | 16 | — | — | — | | | — |
| MTBE | 98 | 98 | 45 | — | 45 | — | — | | | 45 |
| DIB | 2 | 2 | 2 | — | 2 | — | — | | | 2 |

*Units are weight (pounds)

Figure 2:
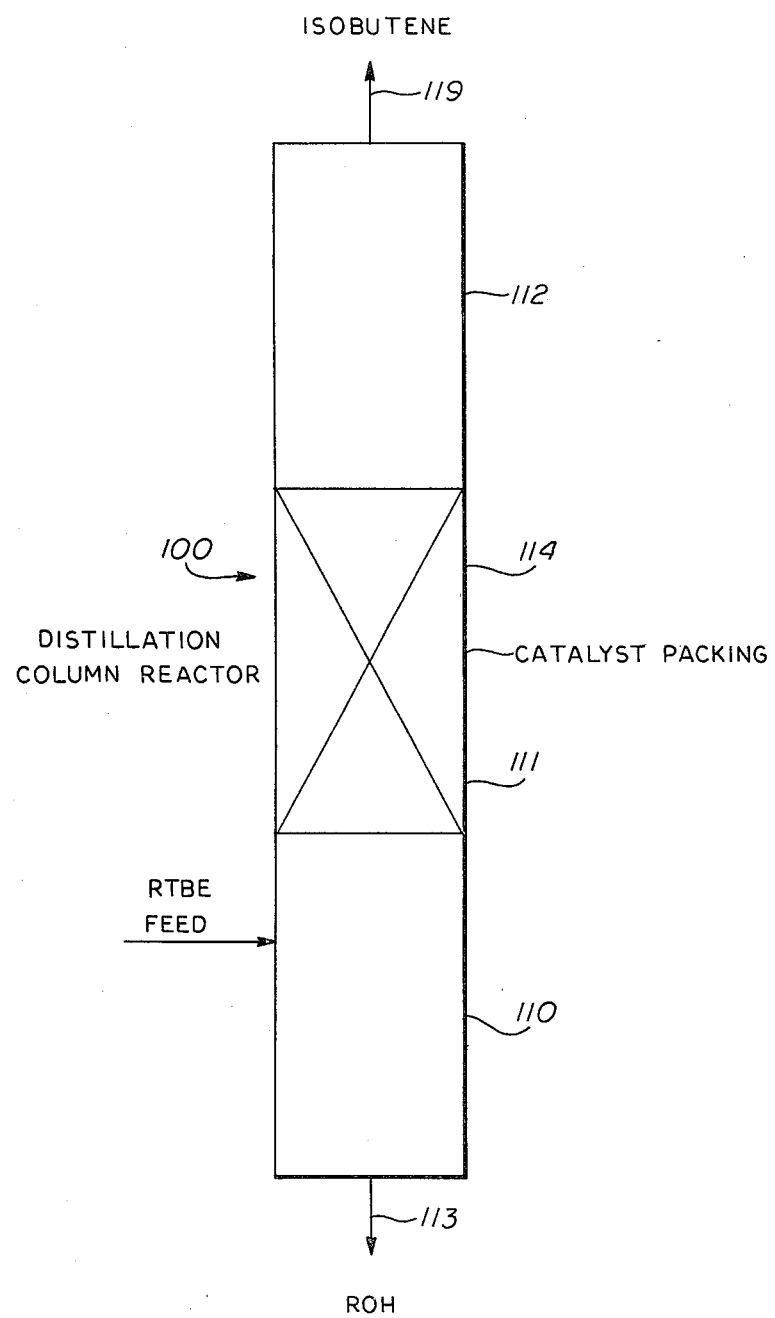
FIG. 2 shows an alternative means for producing high purity isobutylene using concurrent dissociation and distillation.

In FIG. 2, an alternative means is illustrated for several of the procedures described in FIG. 1.

With the proper choice of alcohol (ROH) to produce the corresponding alkyl tertiary butyl ether (RTBE) a single column 100 can be used for the vaporization, dissociation and fractionation. The lower portion 110 of the column is the vaporizer and alcohol stripping section; the middle portion 111 contains the catalyst packing 114 through which the vaporized RTBE (in this case n-propyl tertiary butyl ether) feed passes and dissociates. A feed of 77 wt.% n-propyl tertiary butyl ether was fed at 0.55 LHSV to the reactor. The temperature of the overhead at 25 psig was 30° C. Stream 119 analyzed as 97.8 wt.% isobutene and Stream 113 analyzed as 65.2% n-propyl alcohol, 20.3% diisobutene, 3.2% n-propyl ether, 3.8% n-propyl t-butyl ether, and 7.1% codimers. The type of fixed catalyst bed configuration can be the described catalytic distillation structures which are claimed in U.S. Pat. No. 4,302,356, which is incorporated herein. The upper section 112 is the isobutene fractionation section, producing high purity isobutene via stream 119.

The higher alcohols ($C_3$–$C_6$)OH, e.g., n-propanol do not form azeotropes with the isobutene and are not removed in the overhead. These alcohols 113 are removed from the bottoms of the unit and may be recycled to an etherification.

The main point to be considered in the dissociation, is that it is a preferred vapor phase reaction, wherein the cation acidic exchange resin appears to be a surface contact catalyst for the agitated ether molecules. The presence of a liquid phase is not seen to aid the dissociation and in fact slows the rate somewhat; however, the wetting action of a liquid phase and its washing of the catalyst surface may be of benefit in the long run, i.e., longer catalyst life and less frequent turnarounds. Also the use of the catalytic distillation principles allows greater overall efficiency where the boiling characteristics of the ROH allow this technique to be used.

In any given plant situation, the availability of water capacity, steam, compressors or the like may make the utilization of alternative means, either alone or in combination, the more desirable arrangement.

It should be particularly noted that any of the cation acidic exchange resins can be used, and operate extremely well at what is a very low temperature for the dissociation, compared to the pyrolytic processes taught in the prior art such as U.S. Pat. No. 3,270,081.

Catalysts suitable for the process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents of dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contain sulfur trioxide. The treatment with fuming sulfuric acid is preferably carried out at 0° to 150° C. and the sulfuric acid should contain sufficient sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.25 to 1 mm, although particles from 0.15 mm up to about 1 mm may be employed. The finer catalysts provide high surface area, but also result in high pressure drops through the reactor. The macroreticular form of these catalysts is preferred because of the much larger surface area exposed and the limited swelling which all of these resins undergo in a nonaqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. No.'s 3,784,399; 3,770,567 and 3,849,243.

The invention claimed is:

1. A process for producing high purity isobutene comprising:
    (a) feeding an alkyl tertiary butyl ether to a distillation column reactor into a feed zone at the lower end of a fixed bed acid cation resin packing, said alkyl having three to six carbon atoms,
    (b) concurrently in said distillation column reactor:
        (1) contacting said ether with said fixed bed cation exchange resin packing thereby catalytically dissociating said ether into an isobutene and alcohol having three to six carbon atoms and corresponding to said alkyl, thereby forming a non azeotroping mixture of isobutene and said alcohol, and
        (2) fractionating the resulting mixture in said fixed bed cation exchange resin packing,
    (c) withdrawing isobutene free of alcohol from said distillation column reactor at a point above said packing,
    (d) withdrawing said alcohol from the distillation column reactor at a point below said packing.

2. The process according to claim 1 wherein said ether is n-propyl tertiary butyl ether and the alcohol removed in step (d) is n-propanol.

3. A process for producing high purity isoamylene comprising:
    (a) feeding an alkyl tertiary amyl ether to a distillation column reactor into feed zone at the lower end of a fixed bed cation resin packing, said alkyl having three to six carbon atoms,
    (b) concurrently in said distillation column reactor:
        (1) contacting said ether with said fixed bed cation exchange resin packing thereby catalytically dissociating said ether into isoamylene and an alcohol having three to six carbon atoms and corresponding to said alkyl, thereby forming a non azeotroping mixture of isobutene and said alcohol, and
        (2) fractionating the resulting mixture in said fixed bed cation exchange resin packing,
    (c) withdrawing isoamylene free of alcohol from said distillation column reactor at a point above said packing,
    (d) withdrawing said alcohol from the distillation column reactor at a point below said packing.

4. The process according to claim 3 wherein said ether is n-propyl tertiary amyl ether and the alcohol removed in step (d) is n-propanol.

5. A process for producing high purity diisoolefin comprising:
    (a) vaporizing a feed stream containing alkyl tertiary $C_4$ or $C_5$ ether,
    (b) passing said feed stream in a vaporized state through a first fixed bed cation acidic exchange resin whereby the alkyl tertiary $C_4$ or $C_5$ ether is at least partially dissociated to produce a product stream from said bed, containing isobutene or isoamylene, and an alcohol corresponding to the alkyl radical and unreacted alkyl tertiary $C_4$ or $C_5$ ether,
    (c) removing said alcohol from said product stream,
    (d) passing said alcohol depleted product stream in liquid phase into contact with a second fixed bed cation acidic exchange resin to form a diisoolefin product stream, and
    (e) separating diisoolefin from said diisoolefin product stream.

6. The process according to claim 5 wherein said alkyl is a hydrocarbon radical of $C_1$ to $C_6$ carbon atoms.

7. The process according to claim 6 wherein said alcohol is methanol.

8. The process according to claim 6 wherein said alkyl is methyl.

9. The process according to claim 6 or 8 wherein said alcohol is removed from the dissociation product stream by water washing.

10. The process according to claim 5 wherein the alkyl tertiary $C_4$ or $C_5$ ether is fed at a rate of 0.1 to 20 LHSV.

11. The process according to claim 10 wherein the alkyl tertiary $C_4$ or $C_5$ ether comprises at least 50 wt.% of said feed stream.

12. The process according to claim 6 wherein the alkyl tertiary $C_4$ or $C_5$ ether is alkyl tertiary butyl ether.

13. The process according to claim 6 wherein the alkyl tertiary C$_4$ or C$_5$ ether is alkyl tertiary amyl ether.

14. The process according to claim 1 wherein said alkyl has 4 carbon atoms.

15. The process according to claim 14 wherein said alkyl is tertiary butyl.

16. The process according to claim 1 wherein said alkyl has 5 carbon atoms.

17. The process according to claim 1 wherein said alkyl has 6 carbon atoms.

18. The process according to claim 3 wherein said alkyl has 4 carbon atoms.

19. The process according to claim 18 wherein said alkyl is tertiary butyl.

20. The process according to claim 1 wherein said alkyl has 5 carbon atoms.

21. The process according to claim 1 wherein said alkyl has 6 carbon atoms.

22. The process according to claim 12 wherein said alcohol is methanol and said alkyl is methyl.

23. The process according to claim 12 wherein the alkyl tertiary butyl ether comprises at least 50 wt.% of said feed stream.

24. The process according to claim 23 wherein the alkyl tertiary butyl ether comprises at least 50 wt.% of said feed stream.

25. The process according to claim 13 wherein said alcohol is methanol and said alkyl is methyl.

26. The process according to claim 13 wherein the alkyl tertiary amyl ether is fed at a rate of 0.1 to 20 LHSV.

27. The process according to claim 26 wherein the alkyl tertiary amyl ether comprises at least 50 wt.% of said feed stream.

28. The process according to claim 12 wherein the diisoolefin product stream contains diisobutene and diisobutene is the diisoolefin separated therefrom in step (e).

29. The process according to claim 13 wherein the diisolefin product stream contains diisoamylene and diisoamylene is the diisoolefin separated therefrom in step (e).

30. The process according to claim 6 wherein the alcohol is ethanol.

31. The process according to claim 6 wherein the alcohol is isopropanol.

32. The process according to claim 6 wherein said alcohol is tertiary butanol.

33. The process according to claim 15 wherein said alcohol is tertiary butanol.

34. The process according to claim 19 wherein said alcohol is tertiary butanol.

* * * * *